United States Patent [19]

Miyauchi

[11] Patent Number: 5,152,990
[45] Date of Patent: Oct. 6, 1992

[54] HAIR GROWER

[76] Inventor: Yutaka Miyauchi, No. 5-9, Shigoka-machi, Takasaki-shi, Gunma-ken, Japan

[21] Appl. No.: 644,592

[22] Filed: Jan. 23, 1991

[30] Foreign Application Priority Data

Jan. 31, 1990 [JP] Japan .................................. 2-18877

[51] Int. Cl.⁵ ............................................. A61K 7/06
[52] U.S. Cl. .................................... 424/400; 424/70; 424/195.1; 424/401; 514/880; 514/881
[58] Field of Search ...................... 424/401, 70, 195.1; 514/880, 881

[56] References Cited

U.S. PATENT DOCUMENTS

| | | | |
|---|---|---|---|
| 1,516,562 | 11/1924 | Calabro | 424/195.1 |
| 4,021,577 | 5/1977 | Harich et al. | 424/195.1 |
| 4,195,080 | 3/1980 | Herrera et al. | 424/195.1 |
| 4,933,177 | 6/1990 | Grollier et al. | 424/70 |

FOREIGN PATENT DOCUMENTS 844614  5/1980  Fed. Rep. of Germany .

OTHER PUBLICATIONS

*Heibonsha Dai-Hyakka Jiten,* published by Heibonsha; item 1-1211 (1st ed., Nov. 2, 1984) and item 11-1184 (1st edition, Jun. 28, 1985).
*Genre Japonica Ban-Yu Hyakka Dai-Jiten* published Shogakukan; pp. 57 and 498, 1983.

*Primary Examiner*—Thurman K. Page
*Assistant Examiner*—Amy Hulina
*Attorney, Agent, or Firm*—Beveridge, DeGrandi & Weilacher

[57] ABSTRACT

A hair grower consisting of each extract from the skin of a navel orange, the skin of an iyokan (*Citrus iyo*), the skin of a hassaku (*Citrus hassaku*), the skin of a sweet summer orange, the skin of a lemon, the skin of a mandarin orange, an aloe, all of said extracts are prepared by extracting with sake. The hair grower has an exellent hair-growing effect to positively promote the growth of human hair.

1 Claim, No Drawings

HAIR GROWER

BACKGROUND OF THE INVENTION

1. Field of the Invention

The present invention relates to a hair grower having an excellent hair-growing effect.

2. Description of the Prior Art

The present inventor has already disclosed a novel toilet lotion containing components from citruses and other components (Japanese Patent No. 1,536,922, Japanese Patent Publication No. 20,123/1989). This toilet lotion is very useful because in addition to ordinary functions as a toilet lotion, e.g., astringent and cleansing effects, dampness, and slipperiness to the skin upon its application after facial washing, it has the following secondary effects; that is, it:

(a) has a bleaching action by which a dish cloth and the like can be purified with a color of pure white if they are soiled even with substances which can hardly be washed off;

(b) gives anti-dandruff and antiprustic effects and an effect of preventing the loss of hair by rubbing it into pores of the scalp after shampooing;

(c) is effective for curing stomatitis when held in the mouth;

(d) is effective for lessening the pain and reducing the swelling caused by an insect bite, e.g., sting by bees, caterpillars and the like;

(e) is effective for preventing lacquer poisoning;

(f) is effective for lessening mucus and coughs by oral administration;

(g) protects legs and others from getting pruritus and stickiness caused by stockings and others if it is applied to the legs;

(h) is effective for curing athlete's foot by its application to the legs;

(i) is effective for curing atopic dermatitis by its application to the skin;

(j) serves to stop bleeding from an open sore if it is applied to the open sore;

(k) is a sweet drink;

(l) is effective for curing measles by taking it;

(m) is effective for curing acne when applied; and (n) is effective for curing crazing when applied.

It is considered that the above secondary effects may be due to cooperative and multiplier actions of effective components, e.g. vitamin C and various antimicrobial components in the components from the citruses, moisturizing components in an aloe, and further amino acid contained in sake.

SUMMARY OF THE INVENTION

The present inventor happened to find that among the above secondary effects of the toilet lotion, especially, the effect (b) was so excellent that it might be more than secondary one; the toilet lotion gave not only anti-dandruff and antiprustic effects and an effect of preventing the loss of hair, it was also capable of promoting the growth of human hair positively enough to be worth an excellent hair grower.

Accordingly, it is an object of the present invention to provide a hair grower consisting of:

an extract from the skin of a navel orange, 18.8-20.8% by weight;

an extract from the skin of an iyokan (Citrus iyo), 14.1-15.6% by weight;

an extract from the skin of a hassaku (Citrus hassaku), 18.8-20.8% by weight;

an extract from the skin of a sweet summer orange, 14.1-15.6% by weight;

an extract from the skin of a lemon, 14.1-15.6% by weight;

an extract from the skin of a mandarin orange, 14.1-15.6% by weight; and an extract from an aloe, 1.2-1.3% by weight; all of said extracts being prepared by extracting with sake.

Other objects, features and advantages of the invention will hereinafter become more readily apparent from the following description.

DESCRIPTION OF THE PREFERRED EMBODIMENT

A hair grower having the formulation shown below was prepared in a preferred form of the present invention according a method discussed later and evaluated on its properties as a hair growing agent as also illustrated below.

Formulation

| Components | % by weight |
| --- | --- |
| An extract from a navel orange | 19.75 |
| An extract from a iyokan | 14.82 |
| An extract from a hassaku | 19.75 |
| An extract from a sweet summer orange | 14.82 |
| An extract from a lemon | 14.82 |
| An extract from a mandarin orange | 14.81 |
| An extract from an aloe | 1.23 |
| pH*[1]: | 4.0-6.0 |
| Alcohol number*[2]: | 0.9-1.0 |

*[1] determined according to Japanese Standards of Cosmetic Ingredients - General test method - Test for pH.
*[2] determined according to The Pharmacopoeia of Japan - General test method - Test for alcohol number.

A slight variation in each proportion of the above components is expected in the stages of manufacturing. It was, however, confirmed that some ±5% of the proportion out of the defined range can be tolerated to ensure the same performance and safety of the composition.

Preparation

A navel orange, an iyokan, a Hassaku, a sweet summer orange, a lemon, a mandarin orange, and an aloe were washed with water and sake (refined sake, the first class), and promptly wiped with a dry cloth. All of citruses and the aloe were then respectively subjected to the following treatments:

The skin of the wiped material was peeled off into fragments having a width of 0.8-2.5 cm using a stainless knife; 2 kg of the fragments was charged into a cylinder, into which was poured 3.6 l of sake (the first class refined sake); the fragments was immersed in the sake and allowed to stand at room temperature for 7 days to extract; and the liquid mixture obtained was subjected to filtration using a membrane filter; the filtration was repeated totally five times to prepare an extract.

The extracts thus obtained from the respective materials were incorporated in the foregoing proportion and stirred until an homogeneous mixture was obtained.

Standard for Selection of Citruses

The quality of the hair grower of the present invention is directly influenced by qualitative grades of a navel orange, iyokan, hassaku, and sweet summer orange as starting materials. Desirable citruses as the starting materials of the present invention must therefore be those:

(i) cultivated by the organic cultivation method;
(ii) cultivated in fields with a plant spacing sufficient to permit about 70 trees per 276.8 tsubo (Japanese unit area, i.e., 1 tsubo = approximately 3.3 m$^2$);
(iii) cultivated in fields that are considerably exposed to a see breeze;
(iv) cultivated in fields that are fully exposed to the sun;
(v) planted in fields having a slope facing south;
(vi) cultivated in fields other than those called the farm or the paddy field (citruses grown in the farm or paddy field are of bad quality, and hence they are usually used as canned fruits);
(vii) born from trees putting forth buds in spring, i.e., those grown from buds in summer, autumn, and winter are of bad quality);
(viii) picked between the middle of September and the end of March;
(ix) obtained from adult trees of 17 to 26 or 27 years age (extracts from these trees are very excellent and these trees are lively);
(x) of grades around I and Yo in quality among nine grades, from the highest, Ten, Toku, I, Yo, No, Mi, Ka, Mu, and Shou (which show grades in quality of citruses in Japan);
(xi) selected from those classified by type, color, and skin conditions, i.e., those with an extract of high concentration are desirable;
(xii) born through laborious cares for pulling flowers off trees that bloom from buds in spring,
(xiii) supplied with a plenty of water in summer;
(xiv) having caught no disease and been not covered with frost; and
(xv) being not waxed.

As the starting materials of the hair grower in the present invention, e.g., a navel orange, an iyokan, a hassaku, a sweet summer orange, those having much congruity with the above conditions (i)–(xv) are more desirable.

A navel orange, an iyokan, a hassaku, and a sweet summer orange, all of which were collected according to the above criteria, are exposed to a breeze for 14 days after the collection, and thereafter allowed to stand in a storage at 10°–15° C. under a humidity of about 80–85% for about 20 days until the citruses color pink. This storage is provided with a water bath for keeping the humidity within the above range, and also the storage is airy to supply a plenty of oxygen (air) to the citruses. The navel orange, iyokan, hassaku, and sweet summer orange, which have been stored in such a manner, are extracted with alcohol respectively to obtain extracts for the hair grower of the present invention.

Safety to the Skin (or Scalp)

It is premises that a hair grower must suffice safety to the skin as well as essential hair-growing ability. That is, it is well known that the skin of citruses generally involves not only components effective to the skin, e.g., vitamin C, but also components harmful to the skin, for example, furocoumarins (in particular, bergapten) and limonene, which are the cause of phototoxicity or photo allergy. The treatment of these harmful components would generally be troublesome.

Then a stimulation test, in which a sample is repetitively applied to the skin of rabbits for 30 days, was carried out as one of safety tests. The components of the hair grower in the present example, in particular, each extract from an iyokan (Citrus iyo Hort. et Tanaka (Rutaceae), from a sweet summer orange (Citrus Natsudaidai var. (Rutaceae), from a hassaku (Citrus hassaku Hort. et Tanaka (Rutaceae), and from a navel orange (Citrus sinensis L. Osbeck (Rutaceae), and the hair grower were respectively subjected to the stimulation test. It was confirmed from the test results that the respective extracts from an iyokan, sweet summer orange, hassaku, and navel orange gave a cause of slight inflammation or provoked irritation to the skin, but the hair grower of this example exerted no irritant action on the skin to show that it had safety to the skin. This fact reveals that whereas the citruses themselves may give detriment to the skin, the hair grower of the present invention comprising these citruses is safe to the skin because the detrimental actions of the citruses may be annulled each other.

The safety of the hair grower of the present invention was exemplarily confirmed by the above stimulation test wherein the hair grower was repetitively applied to the skin of rabbits for 30 days. The safety of the hair-grower was also confirmed by all other safety tests including the photo-toxicity test.

Hair-Growing Effect

As symptoms in which loss of hair in pilose regions of a body occurs, many sorts are known, such as masculine alopecia, alopecia areata, and alopecia seborrheica. In this example, however, the hair grower was applied to the scalp of dozens of people irrespective of the sort of alopecia. The hair grower was applied to a hairless portion of the scalp in a rubbing manner, and as a result the several people had new hair which began to grow from pores of the hairless portion and finally covered all of the hairless portion. In addition, the application of the hair grower to a fluffy portion of the scalp resulted in the fact that the fluffy hair which was thin and infirm became thick and firm. The reason why the hair grower of the present invention has such an excellent hair-growing effect has not been clarified. It is, however, presumed that this effect is due to actions of limonene contained in the citruses used for the hair grower.

The proportion of the constituents of the present invention, that is, the proportion of each extract from a navel orange, from an iyokan, from a hassaku, from a sweet summer orange, from a mandarin orange, and from an aloe, is not limited to that in the above example, and is adjustable within the following defined range:

| Components | Proportion (% by weight) |
| --- | --- |
| *An extract from the skin of: | |
| a navel orange | 18.8–20.8 |
| an iyokan (Citrus iyo) | 14.1–15.6 |
| a hassaku (Citrus hassaku) | 18.8–20.8 |
| a sweet summer orange | 14.1–15.6 |
| a lemon | 14.1–15.6 |
| a mandarin orange | 14.1–15.6 |
| an aloe | 1.2–1.3 |

*All of said extracts are prepared by extracting with sake.

As illustrated above, the hair grower according to the present invention provides an excellent hair-growing effect upon application to the human scalp. The hair grower has high safety, and also can be produced by a simple process to permit easy preparation thereof, and thus is economical.

What is claimed is:

1. A hair grower consisting of:
   an extract from the skin of a navel orange, 18.8–20.8% by weight;
   an extract from the skin of an iyokan (Citrus iyo), 14.1–15.6% by weight;
   an extract from the skin of a hassaku (Citrus hassaku), 18.8–20.8% by weight;
   an extract from the skin of a sweet summer orange, 14.1–15.6% by weight;
   an extract from the skin of a lemon, 14.1–15.6% by weight;
   an extract from the skin of a mandarin orange, 14.1–15.6% by weight; and
   an extract from an aloe, 1.2–1.3% by weight; all of said extracts being prepared by extracting with sake.

* * * * *